United States Patent [19]

Kristof et al.

[11] Patent Number: 5,049,568

[45] Date of Patent: Sep. 17, 1991

[54] LIQUID PHARMACEUTICAL COMPOSITION FOR PIPERIDINOALKANOL DERIVATIVES

[75] Inventors: Joseph C. Kristof, Zionsville; DeAnne L. Byers, Indianapolis; Richard A. Knipstein, Carmel, all of Ind.

[73] Assignee: Merrell Dow Pharmaceuticals Inc., Cincinnati, Ohio

[21] Appl. No.: 494,887

[22] Filed: Mar. 9, 1990

Related U.S. Application Data

[63] Continuation of Ser. No. 300,382, Jan. 23, 1989, abandoned.

[51] Int. Cl.⁵ .......................................... A61K 31/445
[52] U.S. Cl. ................................................. 514/317
[58] Field of Search ........................................ 514/317

[56] References Cited

U.S. PATENT DOCUMENTS

| | | | |
|---|---|---|---|
| 3,878,217 | 4/1975 | Carr et al. | 514/317 |
| 4,139,627 | 2/1979 | Lane et al. | 514/315 |
| 4,254,129 | 3/1981 | Carr et al. | 546/239 |
| 4,285,957 | 8/1981 | Carr et al. | 546/239 |
| 4,783,471 | 11/1988 | Carr et al. | 514/317 |
| 4,808,410 | 2/1989 | Sorrentano | 514/317 |
| 4,820,717 | 4/1989 | Masse et al. | 514/317 |
| 4,822,778 | 4/1989 | Aberg et al. | 514/317 |
| 4,870,083 | 9/1989 | Carr et al. | 514/317 |
| 4,912,117 | 3/1990 | Carr et al. | 514/317 |
| 4,929,605 | 5/1990 | Domet et al. | 514/317 |

FOREIGN PATENT DOCUMENTS 0173293  3/1986  European Pat. Off. ............ 514/317

OTHER PUBLICATIONS

Merck Index, 10th Ed, 1983, Entry 8990.
Swinyard and Lowenthal: "Pharmaceutical Necessities," Chapter 67, Remington's Pharmaceutical Sciences, 16th Edition, 1980, p. 1240.

Primary Examiner—Donald G. Daus
Attorney, Agent, or Firm—Louis J. Wille

[57] ABSTRACT

The present invention relates to a liquid pharmaceutical composition comprising (a) a piperidinoalkanol in an amount of from about 2 to about 25 mM; (b) a suitable buffer, selected from the group consisting of gluconic acid buffer, lactic acid buffer, citric acid buffer and acetic acid buffer, in an amount of from about 0.001 to about 0.5 M; and (c) water in an amount of from about 5% to about 99% by weight of the composition.

7 Claims, No Drawings

LIQUID PHARMACEUTICAL COMPOSITION FOR PIPERIDINOALKANOL DERIVATIVES

This is a continuaton of application Ser. No. 300,382, filed Jan. 23, 1989, now abandoned.

BACKGROUND OF THE INVENTION

Various piperidinoalkanol derivatives are disclosed in U.S. Pat. Nos. 3,878,217, 4,254,129, and 4,285,957 as compounds useful as antihistamines, antiallergy agents, and bronchodilators. Included within the scope of these generically defined piperidinoalkanols is o-[4-(1,1dimethylethyl)phenyl]-4-(hydroxydiphenylmethyl)-1piperidinebutanol which is commerci--ally available as a pharmaceutical composition in solid unit dosage form for the treatment of patients with symptoms of seasonal allergic rhinitis. Also included is 4-[1-hydroxy-4-[4-(hydroxydiphenylmethyl) -1-piperidinyl]butyl]-α,60 -dimethylbenzeneacetic acid which is disclosed as an antihistaminic agent in U.S. Patent No. 4,254,129 and which is a known metabolite of α-[4-(1,1-dimethylethyl)phenyl]-4-(hydroxydiphenylmethyl) -1-piperidinebutanol in animals.

In general, these piperidinoalkanol derivatives are only minimally soluble in water and therefore the therapeutically inactive ingredients in a pharmaceutical composition containing one or more of these compounds are very important in providing for their efficient and immediate absorption and bioavailability after oral administration.

A novel liquid pharmaceutical composition is now provided which allows efficient and immediate absorption and bioavailability of these compounds after oral administration thereof.

DETAILED DESCRIPTION OF THE INVENTION

The present invention relates to a pharmaceutical composition for oral administration of various piperidinoalkanol derivatives which are disclosed in U.S. Pat. Nos. 3,878,217, 4,254,129, and 4,285,957, the full disclosures of each patent being incorporated herein by reference. These piperidinoalkanol compounds are useful as antihistamines, antiallergy agents, and bronchodilators and are described by the formulas (1), (2), and (3).

Compounds of formula (1) are those which correspond to the formula

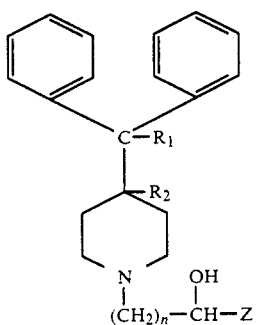

(1)

wherein $R_1$ is hydrogen or hydroxy; $R_2$ is hydrogen; or $R_1$ and $R_2$ taken together form a second bond between the carbon atoms bearing $R_1$ and $R_2$; n is a positive Whole integer of from 1 to 3; Z is thienyl, phenyl or substituted phenyl wherein the substituents on the substituted phenyl may be attached at the ortho, meta, or para positions of the substituted phenyl ring and are selected from the group consisting of a halogen atom, a straight or branched lower alkyl chain of from 1 to 4 carbon atoms, a lower alkoxy group of from 1 to 4 carbon atoms, a di(lower)alkylamino group, or a saturated monocyclic heterocyclic ring selected from the group consisting of pyrolidino, piperidino, morpholino, or N-(lower)alkylpiperizino, or pharmaceutically acceptable acid addition salts thereof.

Compounds of formula (2) are those which correspond to the formula

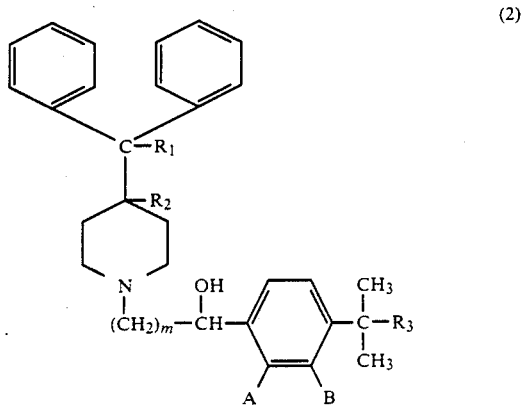

(2)

Wherein $R_1$ represents hydrogen or hydroxy; $R_2$ represents hydrogen; or $R_1$ and $R_2$ taken together form a second bond between the carbon atoms bearing $R_1$ and $R_2$; m is an integer of from 1 to 5; $R_3$ is —$CH_3$, or —$CH_2OH$; each of A and B is hydrogen or hydroxy; with the provisos that at least one of A or B is hydrogen and one of A or B is other than hydrogen when $R_3$ is —$CH_3$; and pharmaceutically acceptable salts and individual optical isomers thereof.

Compounds of formula (3) are those which correspond to the formula

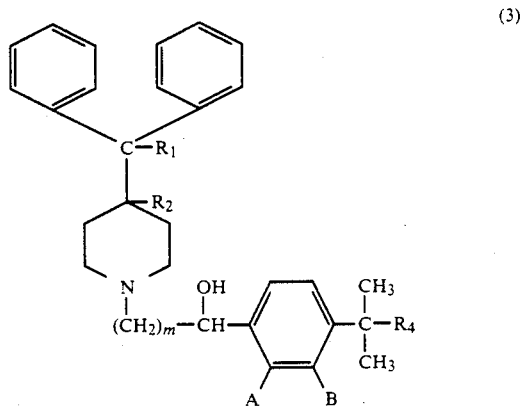

(3)

wherein $R_1$ represents hydrogen or hydroxy; $R_2$ represents hydrogen; or $R_1$ and $R_2$ taken together form a second bond between the carbon atoms bearing $R_1$ and $R_2$; m is an integer of from 1 to 5; $R_4$ is —COOH or —COOalkyl wherein the alkyl moiety has from 1 to 6 carbon atoms and is straight or branched; each of A and B is hydrogen or hydroxy; with the proviso that at least one of A or B is hydrogen; and pharmaceutically acceptable salts and individual optical isomers thereof.

The liquid pharmaceutical compositions provided by the present invention for oral administration comprise (a) a piperidinoalkanol in an amount of from about 2 to about 25 millimolar (mM), (b) a suitable buffer, selected from the group consisting of gluconic acid buffer, lactic acid buffer, citric acid buffer and acetic acid buffer, in an amount of from about 0.001 to about 0.5 molar (M) and (c) water in an amount of from about 5% to about 99% by weight of the composition. In addition, the liquid pharmaceutical compositions of the present invention can optionally contain one or more other therapeutically inert ingredients and/or therapeutically active ingredients as are well known and appreciated in the art of pharmaceutical science.

The liquid pharmaceutical compositions of the present invention are useful in providing a solution of one or more piperidinoalkanols which can be administered orally to a patient in need of treatment with an antihistaminic agent. The preferred piperidinoalkanol is $\alpha$-[4-(1,1dimethylethyl)phenyl]-4-(hydroxydiphenylmethyl)-1piperidinebutanol.

The amount of the piperidinoalkanol present in the liquid pharmaceutical compositions of the present invention can vary from about 2 mM to about 25 mM. The molarity of the piperidinoalkanol present is measured in terms of millimoles per liter of the liquid pharmaceutical composition. As such this amount represents a therapeutically effective dose of the piperidinoalkanol when administered orally according to a standard regimen and unit dosage. The preferred amount of the piperidinoalkanol present in the liquid pharmaceutical composition of the present invention varies from about 2 mM to about 13 mM. Where the desired piperidinoalkanol is $\alpha$-[4-(1,1-dimethylethyl)phenyl]-4-(hydroxydiphenylmethyl)- <1-piperidinebutanol, the most preferred amount of said piperidinoalkanol is about 6 mM, which represents approximately 3 milligrams (mg) per milliliter (mL) or approximately 30 mg per 10 mL dose.

Buffers suitable for use in the liquid pharmaceutical composition of the present invention are those selected from the group consisting of uconic acid buffer, lactic acid buffer, citric acid buffer, and acetic acid buffer.

As used herein, the term "buffer" can mean one or more of the indicated free acids, i.e., guconic acid, lactic acid, citrio acid or acetic acid. The term "buffer" can also mean one or more of the basic derivatives of the indicated free acids such as, for example, sodium guconate, sodium lactate, sodium citrate or sodium acetate. Furthermore, the term "buffer" can mean a mixture of both a free acid and a basic derivative thereof such as, for example, gluconic acid and sodium gluconate, lactic acid and sodium lactate, citric acid and sodium citrate, or acetic acid and sodium acetate. For example, the term "gluconic acid buffer" can mean (i) gluconic acid, (ii) sodium gluconate or (iii) gluconic acid and sodium gluconate.

The preferred buffer for the liquid pharmaceutical composition of the present invention is gluconic acid buffer. It is well known and appreciated by persons skilled in the art that gluconic acid can exist in chemical equilibrium with glucono-$\delta$-lactone. Therefore, it is also well recognized by persons skilled in the art that gluconic acid, such as is encompassed within the meaning of the term "buffer" as defined hereinabove, can be provided by a solution of glucono-$\delta$-lactone.

The preferred buffer for the liquid pharmaceutical composition of the present invention is one which comprises a mixture of a free acid and the basic derivative thereof such as, for example, gluconic acid and sodium gluconate. By adjusting the molar ratios of the free acid and the basic derivative thereof, a buffer with different pH values will be provided. One skilled in the art can, by the proper adjustment of the molar ratios of the free acid and the basic derivative thereof, obtain a liquid pharmaceutical composition characterized by having a particular desired pH.

Liquid pharmaceutical compositions of the present invention which are characterized as having a pH of from about 2 to about 7 are preferred. Liquid pharmaceutical compositions of the present invention which are characterized as having a pH of from about 4 to about 6 are most preferred.

The amount of buffer present in the liquid pharmaceutical compositions of the present invention can vary from about 0.001 M to about 0.5 M. The molarity of the buffer is measured in terms of moles per liter of the liquid pharmaceutical composition. The above range for the molar concentration of the buffer reflects a sum of the number of moles of each buffer moiety present in the liquid pharmaceutical composition. For example, if the desired composition contains both gluconic acid and sodium gluconate, the sum of the number of moles of gluconic acid and the number of moles of sodium gluconate must be from about 0.001 M to about 0.5 M. By way of further example, if the desired composition contains both gluconic acid and lactic acid buffers, the sum of the number of moles of gluconic acid/gluconate and the number of moles of lactic acid/lactate must together be from about 0.001 M to about 0.5 M.

As will be well recognized and appreciated by those skilled on the art of pharmaceutical science, the liquid pharmaceutical compositions of the present invention can contain, in addition to the ingredients specified above, one or more other pharmaceutically acceptable ingredients such as are described generally in *Reminoton's Pharmaceutical Sciences*, 16th edition, Mack Publishing Company, Easton, Pennsylvania (1980). Pharmaceutically acceptable ingredients are therapeutically inert ingredients such as are well known and appreciated in the art. Such therapeutically inert ingredients include: surfactants such as long chain fatty acid esters of polyoxyethylene sorbitan [including polysorbate 80 (also known as Tween 80)], various poloxamers or plutonics [including Pluronic-F68]; conventional carriers such as glycerin, lactose, propylene glycol, polyethylene glycols of various average molecular weights [including PEG 400, 1000 and 3350], and derivatives thereof such as polyoxyethylene fatty acid esters [including polyethylene glycol monostearate], and the like; other excipients such as hydrogenated vegetable oil and the like; sweetening agents such as sorbitol, saccharin, sodium saccharin, sucrose, aspartame, hydrogenated glucose syrup (such as lycasin), mannitol, acesulfame K, monoammonium glycerizin, high fructose corn syrup, invert sugar and the like; coloring agents; flavoring agents; antioxidants; and preservatives and antimicrobials. These additional ingredients together can be present in amounts up to about 90% by weight of the composition. Selection of a particular ingredient or ingredients and the amounts used can be readily determined by one skilled in the art by reference to standard procedures and practices. A preferred combination of additional ingredients include glycerin (99%), propylene glycol, ethanol (95%), and hydrogenated glucose syrup in preferred amounts of from about 10 to about 40% (v/v), from about 10 to about 30% (v/v), from about 1 to about 10% (v/v), and from about 20 to about 50% (v/v), respectively, with about 25% (v/v), 20% (v/v), 5% (v/v), and 35% (v/v), respectively, being most preferred.

Of course, one skilled in the art of pharmaceutical science will recognize and appreciate that the liquid pharmaceutical compositions of the present invention may also contain therapeutically active ingredients other than piperidinoalkanols. It is well known that antihistamines can beneficially be combined with certain decongestants, cough suppressants, expectorants and analgesic agents in a single dosage form. Many examples of such combination therapy products are commercially available. Likewise, the liquid pharmaceutical composition of the present invention may be formulated to contain such decongestants as pseudoephedrine, phenylepherine, and the like; such analgesic agents as aspirin, acetaminophen, ibuprofen and the like; such cough suppressants as dextromethorphan, codeine and the like; and expectorants such as guaifenesin and the like. Selection of one or more therapeutically active ingredients in addition to the piperidinoalkanols and the amounts to be used can be readily determined by one skilled in the art by reference to standard procedures and practices and the recommended dosage levels for the additional therapeutically active ingredients. Furthermore, one skilled in the art of pharmaceutical science will recognize and appreciate that many of these additional therapeutically active ingredients can be utilized in the form of their pharmaceutically acceptable salts. For example, pseudoephedrine HCl, phenylepherine HC1, dextromethorphan HBr, codeine phosphate, codeine sulphate and the like, can be used.

The ingredients of the liquid pharmaceutical composition according to the present invention are formulated according to standard practices and procedures well known in the art of pharmaceutical science using conventional formulation and manufacturing techniques.

In general, the liquid pharmaceutical compositions can be prepared by dissolving the piperidinoalkanol in the desired aqueous buffer solution. The buffer solution is prepared by dissolving the desired buffer in water. Additional ingredients of the desired liquid pharmaceutical composition can be dissolved in the aqueous solution of buffer and piperidinoalkanol. Where a mixture of a free acid and the basic derivative thereof is desired as the buffer, such as, for example, gluconic acid and sodium gluconate, the dissolution of the piperidinoalkanol can be facilitated by dissolving the piperidinoalkanol in an aqueous solution of the free acid. The basic derivative of the free acid can then be added to the solution along with the other ingredients. Dissolution of the piperidinoalkanol in the aqueous buffer solution can be facilitated by first wetting the piperidinoalkanol with a wetting agent such as ethanol.

In a preferred embodiment of the present invention, liquid pharmaceutical compositions of the present invention are made according to Examples 1, 2 and 3. The following examples are illustrative only and are not intended to limit the scope of the present invention in any way.

EXAMPLE 1

LIQUID PHARMACEUTICAL FORMULATION FOR
α-[4-(1,1-DIMETHYLETHYL]PHENYL]-4-[HYDROXYDIPHENYLMETHYL)-1-PIPERIDINEBUTANOL CONTAINING SACCHARIN AND PEG 400

Place 6 grams (g) of o-[4-(1,1-dimethylethyl)-phenyl]4-(hydroxydiphenylmethyl) -1-piperidinebutanol powder in a 2000 milliliter (mL) volumetric flask and wet the powder with 100 mL of ethanol (95%, USP). Add 13.6 mL of a 2.5 molar (M) solution of glucono-δ-lactone in purified water, add an additional 160 mL of purified water and stir until a clear solution results. Add 200 mL of polyethylene glycol 400 and 83 mL of a 2.0 M solution of sodium gluconate in purified water while stirring.

Add 600 mL of lycasin (hydrogenated glucose syrup) while stirring. Add 800 mL of a 10 milligram (mg)/mL solution of saccharin in glycerin while stirring and q.s. to volume (2000 mL) with purified water.

To prepare the saccharin/glycerin solution, heat a mixture of 10 g saccharin powder and 1000 mL of glycerin at 90° C. with constant stirring until dissolved. Allow the solution to cool to room temperature before use.

The resulting liquid pharmaceutical composition has a composition as described in Table 1:

TABLE 1

COMPOSITION OF LIQUID PHARMACEUTICAL FORMULATION CONTAINING SACCHARIN AND PEG 400

| INGREDIENT | AMOUNT IN 2000 mL | COMPOSITION |
|---|---|---|
| Therapeutically Active Ingredient* | 6 g | 3 mg/mL or 6.4 mM |
| Ethanol (95%) | 100 mL | 5% v/v |
| Polyethylene Glycol 400 | 200 mL | 10% v/v |
| Glycerin | 800 mL | 40% v/v |
| Glucono-δ-Lactone | 6.06 g | 0.017M |
| Sodium Gluconate | 36.2 g | 0.083M |
| Lycasin | 600 mL | 30% v/v |
| Saccharin | 8.0 g | 0.4% w/v |
| Water | q.s to 2000 mL | — |

*α-[4-(1,1-dimethylethyl)phenyl]-4-(hydroxydiphenylmethyl)-1-piperidinebutanol

EXAMPLE 2

Liquid Pharmaceutical Formulation For
α-[4-(1,1-Dimethylethyl) Phenyl]-4-(Hydroxydiphenyklmethyl)-1Piperidinebutanol Containing Sodium Saccharin and Propylene Glycol Place 6 grams (g) of α-[4-(1,1-dimethylethyl)phenyl]-(hydroxydiphenylmethyl) -1-piperidinebutanol powder and 8 g of sodium saccharin in a 2000 milliliter (mL) volumetric flask and wet the powders with 100 mL of ethanol (95%, USP). Add 13.6 mL of a 2.5 molar (M) solution of glucono-δ-lactone in purified water, add an additional 160 mL of purified water and stir until a clear solution results. Add 400 mL of propylene glycol and 83 mL of a 2.0 M solution of sodium gluconate in purified water while stirring.

Add 700 mL of lycasin (hydrogenated glucose syrup) and mL of glycerin while stirring and q.s. to volume (2000 mL) with purified water.

The resulting liquid pharmaceutical composition has a composition as described in Table 2:

TABLE 2

COMPOSITION OF LIQUID PHARMACEUTICAL FORMULATION CONTAINING SODIUM SACCHARIN AND PROPYLENE GLYCOL

| INGREDIENT | AMOUNT IN 2000 mL | COMPOSITION |
|---|---|---|
| Therapeutically Active Ingredient* | 6 g | 3 mg/mL or 6.4 mM |
| Ethanol (95%) | 100 mL | 5% v/v |
| Propylene Glycol | 400 mL | 20% v/v |
| Glycerin (99%) | 500 mL | 25% v/v |
| Glucono-δ-Lactone | 6.06 g | 0.017M |
| Sodium Gluconate | 36.2 g | 0.083M |
| Lycasin | 700 mL | 35% v/v |
| Sodium Saccharin | 8.0 g | 0.4% w/v |
| Water | q.s to 2000 mL | — |

*α-[4-(1,1-dimethylethyl)phenyl]-4-(hydroxydiphenylmethyl)-1-piperidinebutanol

EXAMPLE 3

Liquid Pharamaceutical Formulation For
α-[4-(1,1-Dimethylethyl)
Phenyl]-4-(Hydroxydiphenylmethyl)-1-
Piperidinebutanol Containing Sorbitol Place 6 grams (g) of α-[4-(1,1-dimethylethyl)phenyl]-4-(hydroxydiphenylmethyl)-1-piperidinebutanol powder and 8 g of sodium saccharin in a 2000 milliliter (mL) volumetric flask and wet the powders with 60 mL of ethanol (95%, USP). Add 13.6 mL of a 2.5 molar (M) solution of glucono-67-lactone in purified water and add an additional 160 mL of purified water. Add 200 mL of polyethylene glycol 400, 83 mL of a 2.0 M solution of sodium gluconate in purified water and stir until a clear solution results.

Add 800 mL of Sorbitol solution (USP, 70% in purified water) while stirring Add 800 mL of glycerin (99%) while stirring and q.s. to volume (2000 mL) with purified water.

The resulting liquid pharmaceutical composition has a composition as described in Table 3:

TABLE 3

COMPOSITION OF LIQUID PHARMACEUTICAL FORMULATION CONTAINING SORBITOL

| INGREDIENT | AMOUNT IN 2000 mL | COMPOSITION |
|---|---|---|
| Therapeutically Active Ingredient* | 6 g | 3 mg/ml or 6.4 mM |
| Ethanol (95%) | 100 mL | 5% v/v |
| Polyethylene Glycol 400 | 200 mL | 10% v/v |
| Glycerin | 700 mL | 35% v/v |
| Glucono-δ-Lactone | 6.06 g | 0.017M |
| Sodium Gluconate | 36.2 g | 0.083M |
| Sodium Saccharin | 8 g | 0.04% w/v |
| Sorbitol Solution (70%) | 500 mL | 25% v/v |
| Water | q.s to 2000 mL | — |

*α-[4-(1,1-dimethylethyl)phenyl]-4-(hydroxydiphenylmethyl)-1-piperidinebutanol

We claim:

1. A liquid pharmaceutical composition for oral administration comprising (a) α-4-(hydroxydiphenylmethyl) -1-piperidinebutanol in an amount of from 2 to 25 mM; (b) a buffer, selected from the group consisting of gluconic acid buffer, lactic acid buffer, citric acid buffer and acetic acid buffer, in an amount of from 0.001 to 0.5 mM; and (c) water in an amount of from 5% to 99% by weight of the composition.

2. A liquid pharmaceutical composition according to claim 1 wherein α-4-(hydroxydiphenylmethyl) -1-piperidinenbutranol is in an amount of from 2 to about 13 mM.

3. A liquid pharmaceutical composition according to claim 2 wherein α-4-(hydroxydiphenylmethyl) -1-piperidinebutanol is in an amount of about6 mM.

4. A liquid pharmaceutical composition according to claim 3 wherein the buffer is gluconic acid buffer.

5. A liquid pharmaceutical composition according to claim 3 wherein the gluconic acid buffer is in an amount of from, about 0.01 to about 0.15 M.

6. A liquid pharmaceutical composition according to claim 5 which further comprises glycerin (99%) in an amount of about 25% (v/v), propylene glycol in an amount of about 20% (v/v), hydrogenated glucose syrup in an amount of about 35% (v/v) and sodium saccharin in an amount of about 0.4% (w/v).

7. A liquid pharmaceutical composition according to claim 5 which further comprises glycerin (99%) in an amount of about 40% (v/v), polyethylene glycol 400 in an amount of about 10% (v/v), hydrogenated glucose syrup in an amount of about 30% (v/v) and saccharin in an amount of about 0.4% (w/v).

* * * * *